(12) United States Patent
Abumrad et al.

(10) Patent No.: US 10,213,399 B2
(45) Date of Patent: Feb. 26, 2019

(54) COMPOSITIONS AND METHODS OF USE OF β-HYDROXY-β-METHYLBUTYRATE (HMB) FOR MODULATING AUTOPHAGY AND LIPOPHAGY

(71) Applicant: Metabolic Technologies, Inc., Ames, IA (US)

(72) Inventors: Naji Abumrad, Nashville, IA (US); John Rathmacher, Story City, IA (US); Shawn Baier, Polk City, IA (US)

(73) Assignee: Metabolic Technologies, Inc., Ames, IA (US)

( * ) Notice: Subject to any disclaimer, the term of this patent is extended or adjusted under 35 U.S.C. 154(b) by 0 days.

(21) Appl. No.: 15/411,303

(22) Filed: Jan. 20, 2017

(65) Prior Publication Data

US 2017/0209397 A1 Jul. 27, 2017

Related U.S. Application Data

(60) Provisional application No. 62/281,561, filed on Jan. 21, 2016.

(51) Int. Cl.
*A61K 31/19* (2006.01)
(52) U.S. Cl.
CPC .................................. *A61K 31/19* (2013.01)

(58) Field of Classification Search
None
See application file for complete search history.

(56) References Cited

U.S. PATENT DOCUMENTS

2012/0189716 A1 7/2012 Baxter et al.

FOREIGN PATENT DOCUMENTS

| EP | 2647374 | 4/2012 |
|---|---|---|
| WO | 2015049365 | 4/2015 |

OTHER PUBLICATIONS

Giron et al., PLOS ONE (2005), 10(2), pp. e0117520/1-e0117520/20.*

* cited by examiner

*Primary Examiner* — Brian J Davis
(74) *Attorney, Agent, or Firm* — Emily E. Harris

(57) ABSTRACT

The present invention provides a composition comprising HMB. Methods of administering HMB to an animal are also described. HMB is administered to modulate autophagy and lipophagy. HMB is also administered to treat, prevent, inhibit, slow or reduce autophagy-mediated conditions or diseases.

8 Claims, 6 Drawing Sheets

COMPOSITIONS AND METHODS OF USE OF β-HYDROXY-β-METHYLBUTYRATE (HMB) FOR MODULATING AUTOPHAGY AND LIPOPHAGY

This application claims priority to United States Provisional Patent Application No. 62/281,561 filed Jan. 21, 2016 and herein incorporates the provisional application by reference.

BACKGROUND OF THE INVENTION

1. Field

The present invention relates to a composition comprising β-hydroxy-β-methylbutyrate (HMB) and methods of using HMB to treat, prevent or improve diseases or conditions that can benefit from autophagy enhancement and/or modulation.

2. Background

The word autophagy is derived from Greek words that translate into "self-eating". It is a physiologic process that is geared towards recycling of cellular components after destruction of cells in the body. It maintains homeostasis or normal functioning during basal condition, but more importantly during periods of cellular stress. In this regard, autophagy provides an alternate source of intracellular building blocks and substrates that may generate energy to enable continuous cell survival. This process is seen in all eukaryotic systems including fungi, plants, slime mold, nematodes, fruit flies and insects, rodents (laboratory mice and rats), humans.

Autophagy is an essential cellular multistep degradation pathway that terminates in the lysosomes. Autophagy involves the formation of double membrane bound vesicles (autophagosomes) that sequester cytoplasmic cargo consisting of aggregated proteins, defective organelles or lipid droplets for delivery to lysosomes. The process is important for cellular health and for cell survival during stress. Through its function in degrading cytoplasmic protein aggregates and defective organelles, autophagy contributes to maintaining quality control of cellular proteins and organelle function. There is a basal rate of autophagy in most cells that serves to maintain protein homeostasis i.e. "proteostasis" and organelle function and during stress, upregulation of autophagy corrects stress-induced cellular changes to restore proteostasis.

In addition to its housekeeping functions, degradation of protein and lipid via autophagy provides cellular energy. Autophagy is induced by energy challenges such as calorie restriction, fasting or exercise. A specific form of autophagy, called lipophagy, mobilizes lipid stores using autophagosome. The lipids, hydrolyzed by lysosomal acid lipases, are used for energy through beta-oxidation. Autophagic lipid catabolism (lipophagy) is a non-classical mechanism by which cells mobilize lipid stores and maintain cellular homeostasis. Defective lipophagy has been linked to metabolic diseases, such as fatty liver disease, obesity and atherosclerosis. Exercise potently induces autophagy in muscle and heart where it mediates endurance and the beneficial effects of exercise on muscle glucose homeostasis.

Basal autophagy and its upregulation in response to stress are essential for maintenance of tissue health in the muscle, liver, brain, heart, intestine, pancreas, and adipose tissue etc. For example blocking autophagy in the liver by blocking ATG7 or ATG5 results in endoplasmic reticulum stress and induces insulin resistance. Similarly, blocking autophagy by deletion or suppression of the key autophagy protein ATG7 or its downstream mediator ATG5 leads to neuronal death and neurological abnormalities. Autophagy deficits occur with aging, which is often characterized by loss of protein quality control and accumulation of intracellular damage. In part this damage might reflect an age-related decrease in AMPK signaling which reduces autophagy. Autophagy modulates aging through an effect on lipid homeostasis. Enhancing autophagy activity, via overexpression of key autophagy genes or by calorie restriction, promotes anti-aging phenotypes and increases lifespan (20%) in mice.

There is strong evidence for transcriptional and epigenetic control of autophagy. (Pietrocola F., Regulation of Autophagy by Stress-Responsive Transcription Factors. Semin. Cancer Biol. 2013; 23:310-322). In mammals, transcription factor EB (TFEB) and members of the forkhead box protein class O (FOXOs) are master transcriptional regulators of autophagy.

BNIP3 is a transcriptional target of FOXO1 and inhibits the mTOR signaling pathway independent of AMPK. TFEB is transcriptionally induced by CREB activation and is a major transcriptional regulator of autophagy linked genes and also of lysosomal genes.

TFEB appears to exert the most global control over autophagy by regulating multiple steps of autophagy, such as autophagosome biogenesis, substrate targeting, and lysosome degradation by managing expression levels of several autophagy and lysosomal genes. (Settembre C. TFEB Links Autophagy to Lysosomal Biogenesis. Science 2011; 332; 1429-1433). TFEB regulates the autophagic flux by coordinating the expression of genes with functions at all stages of the autophagy process. Further, TFEB regulates lipophagy in adipocytes. (Kaur J, Debnath J. Autophagy at the crossroads of catabolism and anabolism. Nat Rev Mol Cell Biol. 2015; 16(8):461-72).

TFEB activity can be impaired by the age-related accumulation and aggregation of disordered proteins in a variety of metabolic and lysosomal storage diseases. Disruption of normal autophagic processes contributes to the development of metabolic disorders, such as obesity and insulin resistance. Defective lipophagy underlies the basis for the metabolic syndrome of aging.

Autophagy deficits are observed early in Alzheimer's, amyotropic lateral sclerosis (ALS), neurodegeneration, cardiomyopathy, and osteoarthritis. Defective autophagy may also contribute to obesity-associated insulin resistance and autophagy upregulation (example by calorie restriction) improves insulin sensitivity. Autophagy dysfunction is also a major contributor to diseases such as neurodegeneration, liver disease such as hepatitis, hepatic steatosis, cirrhosis, nonalcoholic steatohepatitis (NASH), and fatty liver disease, cancer, autoimmune disorders, metabolic disorders such as diabetes and/or insulin resistance, sarcopenia, and cardiovascular disorders such as stroke, cardiac atrophy, heart attacks, cardiomyopathy, and transient ischemic attacks. Autophagy is defective in humans with muscular dystrophy and studies have shown that this defect contributes to the pathogenesis of the disease. Increased autophagy can be induced by stresses such as nutrient starvation, infection and aging.

Autophagy can be considered somewhat of a double-edged sword; it can act as a tumor suppressor by preventing oncogenic protein substrates, toxic misfolded proteins and damaged organelles that initiate cancer, yet higher autophagic activity has been detected in tumor cells that may assist in the survival and growth of the tumors. Thus, autophagy modulators that act to normalize autophagy can act to prevent too little or too much autophagy and help regulate normal cellular function.

Autophagy is initiated by formation of double or multimembrane vesicles in the cytoplasm forming autophagosomes, which engulf portions of the cytoplasm and organelles. The outer membrane of the autophagosome then fuses with lysosomes, and the inner membrane and the cargo are degraded by hydrolytic enzymes in lysosomes and then its constituents are recycled.

ATG (autophagy-related) proteins have been identified, and are essential for autophagosome biogenesis and maturation. Many of them gather at a double stranded cellular membrane. There are over 31 ATG proteins identified, including two essential ubiquitin-like conjugation systems that control autophagosome biogenesis. The first system results in the covalent attachment of ATG12-ATG5 proteins. In the second system, LC3 protein is conjugated to a lipid molecule, generally to a phosphatidylethanolamine (PE). Both conjugation systems require the function of E1-(ATG7) and E2-like enzymes (ATG3 and ATG10). ATG12-ATG5 stable complex eventually forms a larger complex with ATG16, resulting in the formation of an E3-like enzyme complex that catalyzes LC3-PE conjugation. ATG7 has been implicated in nutrient-mediated autophagy.

Failure of the autophagy process is a contributing factor to muscle disuse atrophy by failing to remove damaged mitochondria. The decrease in mitochondria turnover leads to an accumulation of dysfunctional organs and ensuing muscle damage. Impaired autophagy manifests as muscle atrophy, weakness, and degeneration of muscle myofibers. Autophagy has been shown to be a process that limits muscle damage.

Enhancing autophagy is a new target in developing treatments and prophylactic measures for cardiovascular disease, non-alcoholic fatty liver and insulin resistance. In contrast inhibiting autophagy might be beneficial in cancer by decreasing tumor cell survival to chemotherapeutic agents.

Further, levels of autophagy have been shown to diminish with age, resulting in increased muscle atrophy, decreased strength, decreased muscle function, and sarcopenia. Preserving or modulating the process of autophagy can improve these conditions that result from diminished levels of autophagy.

Aging results in the accumulation of various forms of molecular damage, as seen by malfunctioning organelles, defective enzymes, proteinaceous aggregates and/or DNA mutations. The incidence of chronic diseases, such as neurodegeneration, type II diabetes or cancer rises with age concomitantly with accumulating cellular damage. Normalizing or modulating autophagy acts to attenuate or avoid these age associated processes, thus prolonging an individual's "health span" and potentially their life span. Autophagy and/or lipophagy modulators increase the length of time an individual can lead an active lifestyle without suffering from conditions associated with aging, such as dementia, painful or reduced movement of limbs, diabetes, liver disorders, and/or cardiovascular disorders. These modulators can also decrease the time an individual suffers from infection.

Initial studies suggest that autophagy is regarded as a catabolic process, but recent studies have emphasized the importance of this pathway in sustaining and enabling anabolic pathways. It is now well-established that autophagy-derived nutrients produced from the catabolic degradation all support diverse biosynthetic pathways under basal conditions as well as during starvation. Thus, autophagy is a selective process. It has yet to be determined how autophagy is capable of mobilizing various nutrient pools towards specific anabolic functions. The present invention demonstrates that HMB acts a modulator of basal autophagy as all as autophagy during periods of nutrient excess such as obesity and insulin resistance.

Together, these studies described herein demonstrate a new mode of regulation of autophagy via FoxO3-dependent transcription and also that the autophagic/lysosomal pathway in muscle is regulated coordinately with the proteasomal pathway.

Nutrient starvation, inactivity or denervation, old age, and many diseases including cancer, diabetes, sepsis, renal failure, etc. are all associated with significant muscle loss (atrophy), loss of strength and endurance. The rapid muscle loss is attributed to accelerated protein breakdown secondary to activation of the ubiquitin-proteosomal pathways in the atrophying muscle. Foxo3, a member of the Forkead family of transcription factors, is highly activated under these conditions, and has been implicated as causing the muscle atrophy via transcription of a set of atrophy-related genes ("atrogenes") including critical ubiquitin ligases, as well as stimulating autophagy suggesting the existence of a coordinated regulation of proteasomal and lysosomal systems.

Similarly, during starvation, autophagy selectively degrades lipid droplets, via the process of lipophagy, and this mediated by the expression of TFEB, of which activates the transcription of autophagy and lysosomal biogenesis genes. This factor coordinates the expression of lysosomal hydrolases, membrane proteins and genes involved in autophagy. In the presence of nutrients (and nutrient excess), the activity of these transcriptional factors are modulated by several other proteins, most important of which are mTOR proteins, involving coordinating the regulation of autophagy and lysosomal biogenesis.

HMB

Alpha-ketoisocaproate (KIC) is the first major and active metabolite of leucine. A minor product of KIC metabolism is β-hydroxy-β-methylbutyrate (HMB). HMB has been found to be useful within the context of a variety of applications. Specifically, in U.S. Pat. No. 5,360,613 (Nissen), HMB is described as useful for reducing blood levels of total cholesterol and low-density lipoprotein cholesterol. In U.S. Pat. No. 5,348,979 (Nissen et al.), HMB is described as useful for promoting nitrogen retention in humans. U.S. Pat. No. 5,028,440 (Nissen) discusses the usefulness of HMB to increase lean tissue development in animals. Also, in U.S. Pat. No. 4,992,470 (Nissen), HMB is described as effective in enhancing the immune response of mammals. U.S. Pat. No. 6,031,000 (Nissen et al.) describes use of HMB and at least one amino acid to treat disease-associated wasting.

The use of HMB to suppress proteolysis originates from the observations that leucine has protein-sparing characteristics. The essential amino acid leucine can either be used for protein synthesis or transaminated to the α-ketoacid (α-ketoisocaproate, KIC). In one pathway, KIC can be oxidized to HMB and this account for approximately 5% of leucine oxidation. HMB is superior to leucine in enhancing muscle mass and strength. The optimal effects of HMB can be achieved at 3.0 grams per day when given as calcium salt of HMB, or 0.038 g/kg of body weight per day, while those of leucine require over 30.0 grams per day.

Once produced or ingested, HMB appears to have two fates. The first fate is simple excretion in urine. After HMB is fed, urine concentrations increase, resulting in an approximate 20-50% loss of HMB to urine. Another fate relates to the activation of HMB to HMB-CoA. Once converted to HMB-CoA, further metabolism may occur, either dehydration of HMB-CoA to MC-CoA, or a direct conversion of HMB-CoA to HMG-CoA, which provides substrates for intracellular cholesterol synthesis. Several studies have shown that HMB is incorporated into the cholesterol synthetic pathway and could be a source for new cell membranes that are used for the regeneration of damaged cell membranes. Human studies have shown that muscle damage following intense exercise, measured by elevated plasma CPK (creatine phosphokinase), is reduced with HMB supplementation within the first 48 hrs. The protective effect of HMB lasts up to three weeks with continued daily use. Numerous studies have shown an effective dose of HMB to be 3.0 grams per day as CaHMB (calcium HMB) (~38 mg/kg body weight-day$^{-1}$). HMB has been tested for safety, showing no side effects in healthy young or old adults. HMB in combination with L-arginine and L-glutamine has also been shown to be safe when supplemented to AIDS and cancer patients.

Recently, HMB free acid, a new delivery form of HMB, has been developed. This new delivery form has been shown to be absorbed quicker and have greater tissue clearance than CaHMB. The new delivery form is described in U.S. Patent Publication Serial No. 20120053240 which is herein incorporated by reference in its entirety.

It has been surprisingly and unexpectedly discovered that HMB modulates both autophagy and lipophagy. The present invention comprises a composition of HMB and methods of use of HMB to result in normalized or modulated autophagic processes. The processes are involved in protecting humans and other animals from the consequences of excessive muscle wasting and atrophy which are common with nutrient deprivation and excesses, as well as activating lipolytic pathways which are necessary for providing energy. It is well established that nutrient excess as well as several diseases (e.g. sepsis, cancer, etc.) are associated with inhibition of lipolysis, and in this regard, HMB modulate the autophagy pathways to mobilize the adipose tissue stores and enhance beta oxidation thus providing energy. HMB's role as an autophagy and lipophagy modulator is depicted in FIG. 1.

SUMMARY OF THE INVENTION

One object of the present invention is to provide a composition for use in modulating autophagy.

A further object of the present invention is to provide a composition for use increasing expression of ATG7.

A further object of the present invention is to provide a composition for use in modulating lipophagy.

An additional object of the present invention is to provide a composition for use in enhancing CREB phosphorylation.

Another object of the present invention is to provide a composition for use in inducing the transcription factor TFEB to upregulate autophagy genes.

Another object of the present invention is to provide methods of administering a composition for use in modulating autophagy.

An additional object of the present invention is to provide methods of administering a composition for increasing expression of ATG7.

Another object of the present invention is to provide methods of administering a composition for use in modulating lipophagy.

A further object of the present invention is to provide methods of administering a composition for use in enhancing CREB phosphorylation.

Another object of the present invention is to provide methods of administering a composition for use in modulating the expression or activity of the transcription factor TFEB.

Another object of the present invention is to provide methods of administering a composition for use in preventing, reducing, inhibiting, treating or slowing autophagy-related conditions and diseases.

These and other objects of the present invention will become apparent to those skilled in the art upon reference to the following specification, drawings, and claims.

The present invention intends to overcome the difficulties encountered heretofore. To that end, a composition comprising HMB is provided. The composition is administered to a subject in need thereof. All methods comprise administering to the animal HMB. The subjects included in this invention include humans and non-human mammals.

DETAILED DESCRIPTION OF THE INVENTION

Figure 1:
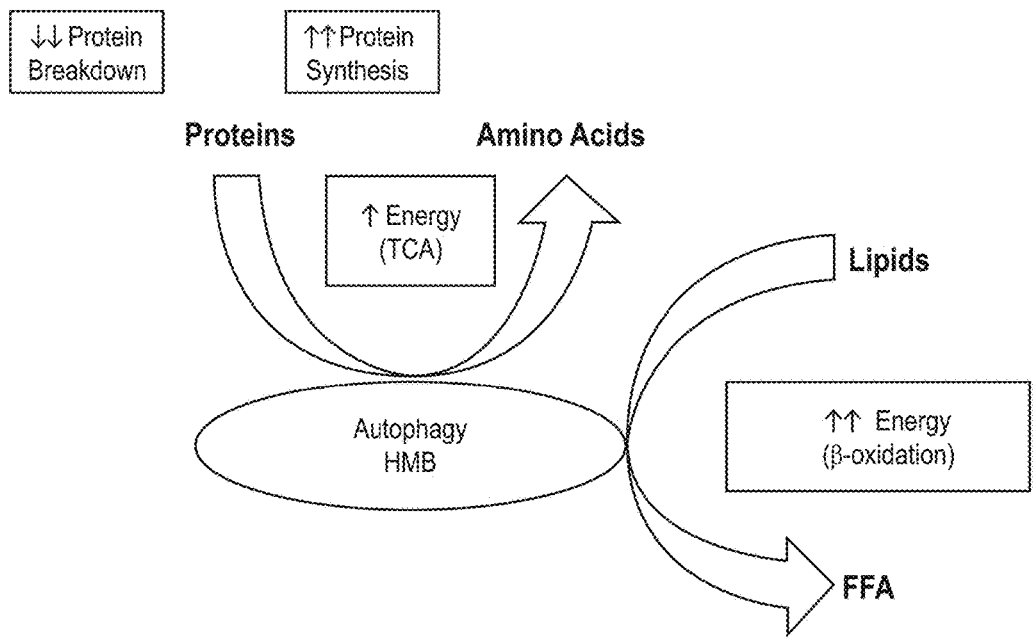
FIG. 1 is an illustration depicting HMB's role in autophagy and lipophagy.

It has been surprisingly and unexpectedly discovered that HMB modulates both autophagy and lipophagy in both muscle cells and adipocytes. The present invention comprises a composition of HMB and methods of use of HMB to result in modulated autophagy in both of these cell types. Further, has been unexpectedly and surprisingly discovered that HMB modulates both basal autophagy and autophagy during a period of nutrient excess. In addition, HMB acts on at least two pathways related to autophagy: the BNIP3 pathway related to the transcription factor FOXO1 and CREB activation related to the transcription factor TFEB.

HMB acts as an autophagy-modulator in more than one system; the data demonstrates that it modulates autophagy in adipose tissue and in muscle. As it has been observed that correction of autophagy in one system affects other systems, HMB coordinates or modulates autophagy among various tissues. This coordination between various tissues is also known as cross-talk, thus HMB acts as a cross-talk agent between tissues.

The compositions and methods of this invention are directed to animals, including human and non-human animals. The animal may be healthy or may be suffering from a disease or condition. The composition and methods of this invention are directed to any use for which there is a benefit from enhancing or modulating autophagy. By way of non-limiting examples, modulating or enhancing autophagy is beneficial during aging, to slow or reverse muscle atrophy, to prevent or treat sarcopenia, and to attenuate muscle destruction, including muscle destruction that is exercise-induced. Other benefits of modulating autophagy and/or lipophagy include reducing or preventing neuromuscular diseases, neurodegenerative diseases, cardiovascular diseases, metabolic diseases, liver diseases, infection, and cancer, including tumor formation.

Neurodegenerative diseases include but are not limited to Alzheimer's disease, dementia, Amyotrophic lateral sclerosis, Huntington's disease and Parkinson's disease.

Cardiovascular diseases include but are not limited to stroke, cardiac atrophy, heart attack, cardiomyopathy, atherosclerosis and transient ischemic attacks.

Liver diseases include but are not limited to hepatitis, hepatic steatosis, cirrhosis, nonalcoholic fatty liver disease, and nonalcoholic steatohepatitis (NASH).

Metabolic diseases that result from nutrient excess include but are not limited to obesity, type II diabetes, and insulin resistance.

Promoting longevity means increasing the expected lifespan of an animal.

Increasing the length of time an animal can lead an active lifestyle includes increasing the length of time an active lifestyle can be maintained without being impeded or prevented by conditions associated with old age such as, by way of non-limiting example, dementia, painful or reduced movement of limbs, and decreased cardiovascular function.

Health span includes the period of an individual's life during which they are generally healthy and free from serious or chronic illnesses health span is an extension of a period of health.

β-hydroxy-β-methylbutyric acid, or β-hydroxy-isovaleric acid, can be represented in its free acid form as $(CH_3)_2(OH)CCH_2COOH$. The term "HMB" refers to the compound having the foregoing chemical formula, in both its free acid and salt forms, and derivatives thereof. While any form of HMB can be used within the context of the present invention, preferably HMB is selected from the group comprising a free acid, a salt, an ester, and a lactone. HMB esters include methyl and ethyl esters. HMB lactones include isovalaryl lactone. HMB salts include sodium salt, potassium salt, chromium salt, calcium salt, magnesium salt, alkali metal salts, and earth metal salts.

Methods for producing HMB and its derivatives are well-known in the art. For example, HMB can be synthesized by oxidation of diacetone alcohol. One suitable procedure is described by Coffman et al., *J. Am. Chem. Soc.* 80: 2882-2887 (1958). As described therein, HMB is synthesized by an alkaline sodium hypochlorite oxidation of diacetone alcohol. The product is recovered in free acid form, which can be converted to a salt. For example, HMB can be prepared as its calcium salt by a procedure similar to that of Coffman et al. (1958) in which the free acid of HMB is neutralized with calcium hydroxide and recovered by crystallization from an aqueous ethanol solution. The calcium salt of HMB is commercially available from Metabolic Technologies, Ames, Iowa.

More than 2 decades ago, the calcium salt of HMB was developed as a nutritional supplement for humans. Studies have shown that 38 mg of CaHMB per kg of body weight appears to be an efficacious dosage for an average person.

The molecular mechanisms by which HMB decreases protein breakdown and increases protein synthesis have been reported. Eley et al conducted in vitro studies which have shown that HMB stimulates protein synthesis through mTOR phosphorylation. Other studies have shown HMB decreases proteolysis through attenuation of the induction of the ubiquitin-proteosome proteolytic pathway when muscle protein catabolism is stimulated by proteolysis inducing factor (PIF), lipopolysaccharide (LPS), and angiotensin II. Still other studies have demonstrated that HMB also attenuates the activation of caspases-3 and -8 proteases.

In most instances, the HMB utilized in clinical studies and marketed as an ergogenic aid has been in the calcium salt form. Recent advances have allowed the HMB to be manufactured in a free acid form for use as a nutritional supplement. Recently, a new free acid form of HMB was developed, which was shown to be more rapidly absorbed than CaHMB, resulting in quicker and higher peak serum HMB levels and improved serum clearance to the tissues.

HMB free acid may therefore be a more efficacious method of administering HMB than the calcium salt form, particularly when administered directly preceding intense exercise. One of ordinary skill in the art, however, will recognize that this current invention encompasses HMB in any form.

HMB in any form may be incorporated into the delivery and/or administration form in a fashion so as to result in a typical dosage range of about 0.5 grams HMB to about 30 grams HMB.

The term administering or administration includes providing a composition to a mammal, consuming the composition and combinations thereof.

When the composition is administered orally in an edible form, the composition is preferably in the form of a dietary supplement, foodstuff or pharmaceutical medium, more preferably in the form of a dietary supplement or foodstuff. Any suitable dietary supplement or foodstuff comprising the composition can be utilized within the context of the present invention. One of ordinary skill in the art will understand that the composition, regardless of the form (such as a dietary supplement, foodstuff or a pharmaceutical medium), may include amino acids, proteins, peptides, carbohydrates, fats, sugars, minerals and/or trace elements.

In order to prepare the composition as a dietary supplement or foodstuff, the composition will normally be combined or mixed in such a way that the composition is substantially uniformly distributed in the dietary supplement or foodstuff. Alternatively, the composition can be dissolved in a liquid, such as water or included in an emulsion.

The composition of the dietary supplement may be a powder, a gel, a liquid or may be tabulated or encapsulated.

Although any suitable pharmaceutical medium comprising the composition can be utilized within the context of the present invention, preferably, the composition is combined with a suitable pharmaceutical carrier, such as dextrose or sucrose.

Furthermore, the composition of the pharmaceutical medium can be intravenously administered in any suitable manner. For administration via intravenous infusion, the composition is preferably in a water-soluble non-toxic form. Intravenous administration is particularly suitable for hospitalized patients that are undergoing intravenous (IV) therapy. For example, the composition can be dissolved in an IV solution (e.g., a saline or glucose solution) being administered to the patient. Also, the composition can be added to nutritional IV solutions, which may include amino acids, peptides, proteins and/or lipids. The amounts of the composition to be administered intravenously can be similar to levels used in oral administration. Intravenous infusion may be more controlled and accurate than oral administration.

Methods of calculating the frequency by which the composition is administered are well-known in the art and any suitable frequency of administration can be used within the context of the present invention (e.g., one 6 g dose per day or two 3 g doses per day) and over any suitable time period (e.g., a single dose can be administered over a five minute time period or over a one hour time period, or, alternatively, multiple doses can be administered over an extended time period). HMB can be administered over an extended period of time, such as weeks, months or years. The composition can be administered in individual servings comprising one or more than one doses (individual servings) per day, to make a daily serving comprising the total amount of the composition administered in a day or 24 hour period.

Any suitable dose of HMB can be used within the context of the present invention. Methods of calculating proper doses are well known in the art.

EXPERIMENTAL EXAMPLES

The following examples will illustrate the invention in further detail. It will be readily understood that the composition of the present invention, as generally described and illustrated in the Examples herein, could be synthesized in a variety of formulations and dosage forms. Thus, the following more detailed description of the presently preferred embodiments of the methods, formulations and compositions of the present invention are not intended to limit the scope of the invention, as claimed, but it is merely representative of the presently preferred embodiments of the invention.

Autophagy in Muscle Cells

Figure 2:
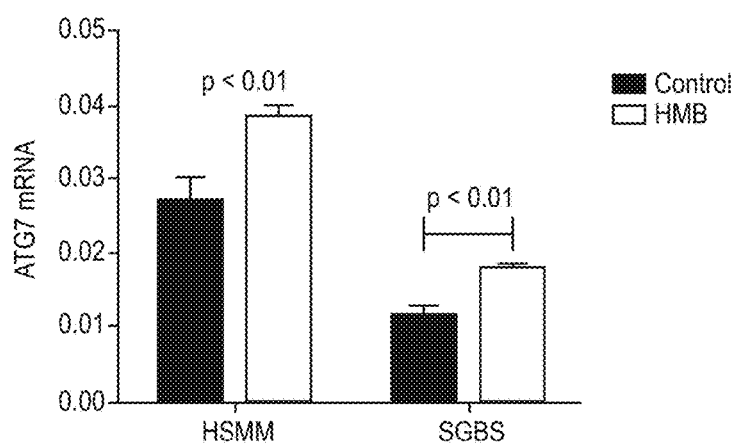
FIG. 2 is a graph showing expression of ATG7 in muscle myotubes.

Cultured primary human skeletal muscle cells (HSMM, Lonza) were grown to confluence and differentiated into myotubes. The cells were then supplemented with HMB (1 mM) for 4 days (n=6 for treatment or control groups) with a medium change every other day. Gene expression (mRNA) was determined at the end of the treatment by quantitative polymerase chain reaction (qPCR). For normalization, the mRNA signal was adjusted to the co-amplified signal of the ribosomal protein 36B4. Significant (p<0.01) upregulation of ATG7 gene expression was observed. The results are shown in FIG. 2.

Autophagy in Adipocytes and Preadipocytes

Example 1

Figure 3A:
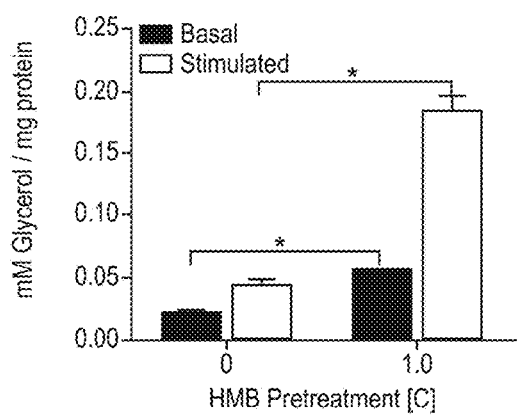
FIG. 3A is graph showing isoproterenol-stimulated and basal lipolysis in differentiated adipocytes.
Figure 3B:
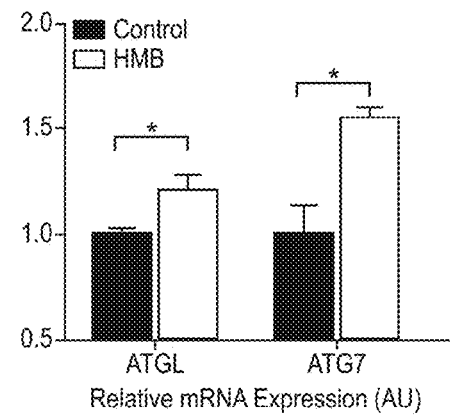
FIG. 3B is a graph showing ATGL and ATG7 relative mRNA expression in differentiated adipocytes.

Differentiated adipocytes were treated with HMB in regular growth medium for determination of lipolysis and gene expression. The adipocytes were pretreated for 48 hours with 1 mM HMB (n=4), resulting in basal and 1 uM isoproterenol stimulated lipolysis (FIG. 3A). Gene expression of adipose triglyceride lipase (ATGL) and autophagy related protein (ATG7) were significantly increased following 96 hours of treatment (FIG. 3B, n=6) *p<0.05. This indicates that HMB activates not only classical triglyceride lipolysis but also autophagy-mediated mobilization of cellular lipid stores (lipophagy).

Example 2

Figure 4:
FIG. 4 is a picture showing lipid droplet accumulation in human subcutaneous preadipocytes.
Figure 5A:
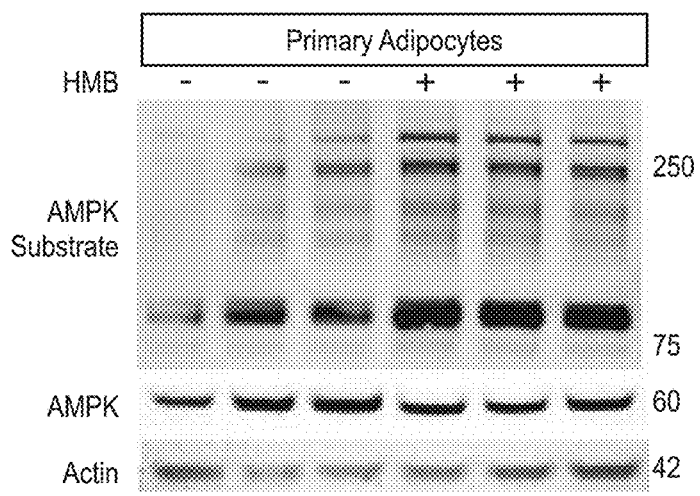
FIGS. 5A and 5B show AMPK activation in primary human adipocytes.
Figure 5B:
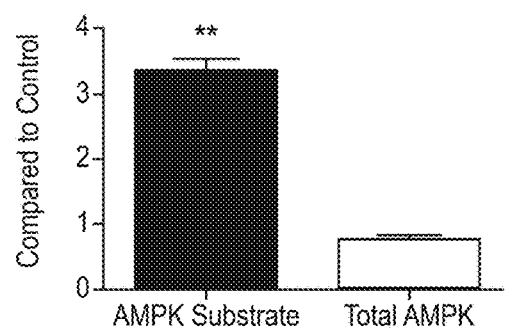

A line of subcutaneous preadipocytes isolated from normal humans (non-diabetic controls) was used. These cells differentiate well (see FIG. 4) and provide a good in vitro model for studying effects of HMB on lipophagy. The subcutaneous human adipocytes showed efficient lipid droplet accumulation at 14 days post confluence (FIG. 4). Differentiated adipocytes (14 days post confluence) were treated for 4 days with 1 mM HMB supplemented in normal growth medium. Lysates were probed with an antibody (Cell Signal Technologies) directed against AMPK phosphorylated substrates (consensus motif LCRXXpS/pT) to obtain a broad evaluation of AMPK activation and total AMPK levels were also measured. A striking, significant increase in AMPK substrate phosphorylation intensity in adipocytes treated with HMB (FIG. 5) while total AMPK levels were not significantly changed. FIG. 5A shows primary adipocytes treated for 96 hours with 1 mM HMB. The cells were lysed and probed for phosphorylated targets of AMPK and for total AMPK levels (FIG. 5B). Densitometry results demonstrated a significant increase in phosphorylation of AMPK targets. n=3, **p<0.01. This effect was not observed in similarly treated HEK293 cells (data not shown) indicating that HMB regulation of AMPK is cell specific and that it contributes to upregulating autophagy and the increase in lipolysis in HMB treated adipocytes.

Figure 6:
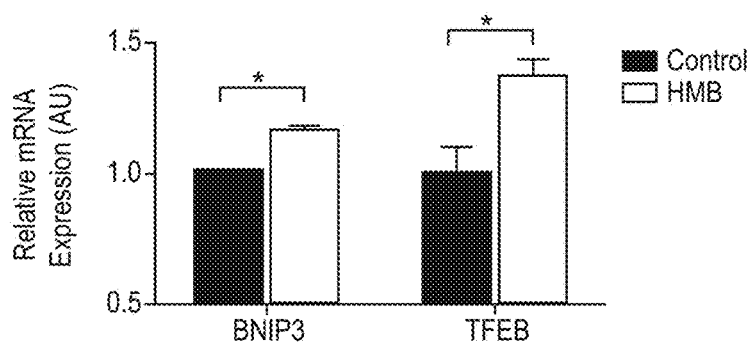
FIG. 6 shows gene expression of autophagy-related transcription factors.

Gene expression analysis from HMB treated primary adipocytes revealed increased mRNA levels for two key transcription factors that upregulate autophagy: BNIP3 and TFEB. FIG. 6 shows expression of these autophagy-related transcription factors in human primary adipocytes following treatment with 1 mM HMB for 96 hours. n=3; *p<0.05. These transcription factors represent two different autophagy pathways. BNIP3 is a transcriptional target of Foxo1 and inhibits the mTOR signaling pathway independent of AMPK and TFEB is transcriptionally induced by CREB activation and is a major transcriptional regulator of autophagy linked genes and also of lysosomal genes.

Example 3

Figure 7:
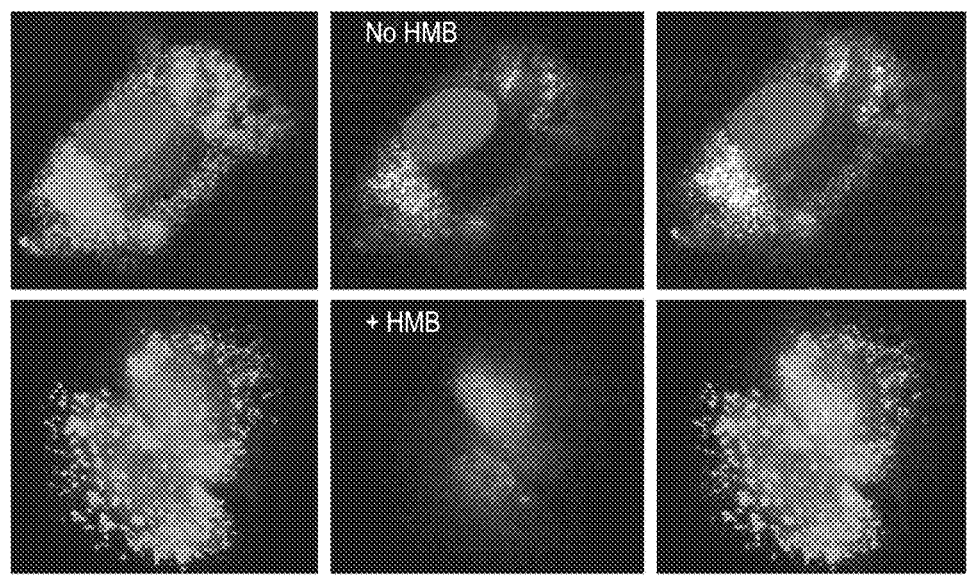
FIG. 7 is a picture visualizing the effect of HMB on autophagy in preadipocytes.

A primary adipocyte cell based assay for visualizing HMB activated lipophagy was developed. Primary preadipocytes were cultured on glass coverslips and treated with HMB for four days in regular growth medium. Cells were fixed and mounted with DAPI-containing medium and imaged with 60× objective. Autophagy vesicles are in red with degradation of green signal indicative of autophagy activation (FIG. 7). Nuclei are stained in blue (FIG. 7). A dual-labeled LC3 retroviral expression contrast was used to generate recombinant retrovirus using 293GPG cells. Primary preadipocytes were infected with the viral particles and, starting with four days after infection, selected with geneticin for two weeks prior to the imaging experiments. The LC3 fusion construct labels the autophagosomes and harbors dual signals; DsRed and GFP green probes. In the basal state there is co-localization of the green and red signals resulting in a yellow signal in the merged panel (FIG. 7 top panel with no HMB). When autophagy is activated, the GFP probe is cleaved from LC3 by ATG4 and degraded resulting in loss of the green signal and in absence of the co-localization in the merged panel. The initial studies used preadipocytes infected with the LC3 containing retrovirus and treated or not treated for 4 days with 1 mM HMB (FIG. 7, top: no HMB, bottom +HMB). Loss of green signals and absence of green/red co-localization after HMB treatment were observed. Additionally, significant increases in the size of autophagic puncta were observed (FIG. 7).

Lysates from HMB-treated muscle (HSMM) and adipocytes (SGBS) were analyzed using a phosphor protein array.

Figure 8:
FIG. 8 is a chart showing the results of a phosphor protein assay in HMB treated muscle (HSMM) and adipocytes (SGBS).

Many mTOR targets were regulated in both cell system (FIG. 8). Increases in CREB phosphorylation on serine 133 on a signaling protein array using SGBS adipocytes treated HMB was seen (FIG. 8). Thus, the activating phosphorylation of CREB at S133 mediates induction of TFEB in these adipocytes and this pathway results in the upregulation of autophagy.

As shown in FIG. 8, HMB treatment of SGBS adipocytes resulted in enhanced CREB phosphorylation, which induces the transcription factor TFEB to upregulate autophagy genes. Enhanced Yes kinase phosphorylation was demonstrated in these cells, along with enhanced HSP27 phosphorylation which leads to stimulated autophagy and enhanced lipid droplet clearance. Reduced activity of the mTOR pathway was seen, which results in disinhibition of autophagy. Reduced activation of pSTAT3 and p53 were seen, which enhances autophagy.

Also in FIG. 8, HMB treatment of muscle cells (HSMM) led to inhibition of mTOR activity as shown from significant reduction of a number of mTOR targets: p70 S6 kinase at several threonine p-sites, RSK 1/2/3 at the mTOR site (S473). The data shows reduced activation of the autophagy inhibitors STAT3 and p53.

AMPK activation by HMB inhibits the mTOR pathway, thus disinhibiting autophagy.

Figure 9:
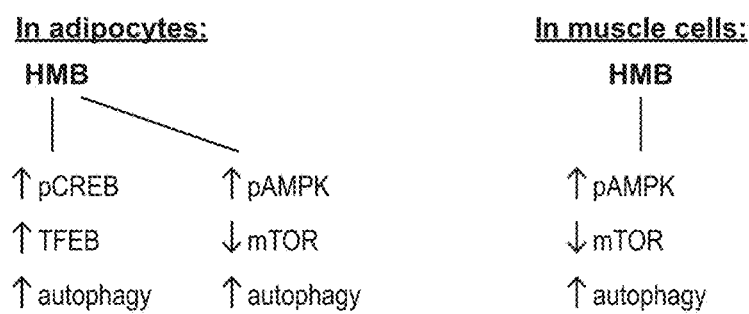
FIG. 9 is an illustration summarizing the effects of HMB on autophagy in adipocytes and in muscle cells.

Taken together, several pathways by which HMB influences autophagy and/or lipophagy have been identified. These pathways have been depicted in the illustration in FIG. 9.

These experimental examples demonstrate that HMB modulates autophagy and lipophagy in muscle, preadipocyte and adipocyte cells. This modulation of autophagy and lipophagy results in treatment, prevention, inhibition, reduction or slowing of autophagy and lipophagy related diseases and conditions, including cancer, neurodegenerative disease, cardiovascular disease, liver disease, infection, muscle disease and disorders, and metabolic disorders including obesity, insulin resistance, and type II diabetes. Use of HMB as an autophagy and lipophagy modulator also increases lifespan and health span, slows aging, and increases the time an individual can lead an active lifestyle.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

The invention claimed is:

1. A method of modulating autophagy in a mammal comprising administering to the mammal from about 0.5 g to about 30 g of β-hydroxy-β-methylbutyric acid (HMB), wherein upon said administration of said HMB to the mammal, autophagy is modulated in adipocytes.

2. A method of modulating autophagy in a mammal comprising administering to the mammal from about 0.5 g to about 30 g of β-hydroxy-β-methylbutyric acid (HMB), wherein upon said administration of said HMB to the mammal, autophagy is modulated and wherein the type of autophagy that is modulated is lipophagy.

3. The method of claim 1, wherein autophagy is modulated during nutrient excess.

4. The method of claim 1, wherein basal autophagy is modulated.

5. The method of claim 1, wherein said HMB is selected from the group consisting of its free acid form, its salt, its ester and its lactone.

6. The method of claim 5, wherein said salt is selected from the group consisting of a sodium salt, a potassium salt, a magnesium salt, a chromium salt, and a calcium salt.

7. The method of claim 1, wherein the modulation of autophagy results in the treatment, inhibition, or reduction of an autophagy-related disease or condition selected from the list consisting of cardiovascular disease, type II diabetes, neurodegenerative disorders, metabolic syndromes, liver disease, reduced metabolic rate, muscle disease, osteoarthritis, sarcopenia, cancer, obesity, and insulin resistance.

8. The method of claim 2, wherein the modulation of lipophagy by the administration of HMB results in the treatment, inhibition, or reduction of an autophagy-related disease or condition selected from the list consisting of cardiovascular disease, type II diabetes, neurodegenerative disorders, metabolic syndromes, liver disease, reduced metabolic rate, muscle disease, osteoarthritis, sarcopenia, cancer, obesity, and insulin resistance.

* * * * *